United States Patent [19]

Noordam

[11] Patent Number: 4,514,547
[45] Date of Patent: Apr. 30, 1985

[54] 2-HYDROXYPROPANE SULPHONIC ACID DERIVATIVES: THEIR PREPARATION AND CURABLE COMPOSITIONS THEREOF

[75] Inventor: Arend Noordam, Amsterdam, Netherlands

[73] Assignee: Shell Oil Company, Houston, Tex.

[21] Appl. No.: 489,435

[22] Filed: Apr. 28, 1983

[30] Foreign Application Priority Data

Jul. 6, 1982 [GB] United Kingdom ............... 8219521

[51] Int. Cl.$^3$ .................................... C08L 63/02
[52] U.S. Cl. ........................ 525/510; 525/481; 525/523; 528/109; 260/503; 260/505 C; 260/505 N
[58] Field of Search ............. 528/109; 525/510, 523, 525/481; 260/503, 505 C; 423/512 A, 517, 519

[56] References Cited

U.S. PATENT DOCUMENTS

| 2,633,458 | 3/1953 | Shokal ........................... 260/45.2 |
| 4,317,757 | 3/1982 | Kooijmans ........................ 525/523 |
| 4,379,872 | 4/1983 | Ishikura .......................... 525/523 |

FOREIGN PATENT DOCUMENTS

| 542521 | 6/1957 | Canada ........................... 525/510 |
| 46-12149 | 3/1971 | Japan ............................. 528/109 |
| 983049 | 2/1965 | United Kingdom . |
| 1059984 | 2/1967 | United Kingdom . |
| 1310672 | 3/1973 | United Kingdom . |
| 1530649 | 11/1978 | United Kingdom . |

Primary Examiner—Theodore E. Pertilla

[57] ABSTRACT

The invention provides 2-hydroxypropane sulphonic acid derivatives of general formula

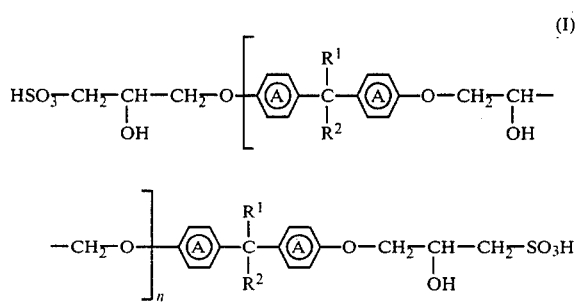

wherein n is a number having an average value from 0 to 12, Ⓐ denotes saturation or aromatic unsaturation in an associated carbocyclic ring and the or each of the $R^1$ and $R^2$ groups are independently selected from hydrogen and $C_{1-12}$ alkyl groups provided that each —C($R^1$)($R^2$)— group contains not more than 13 carbon atoms; and salts thereof; a process for their preparation and curable compositions containing them.

9 Claims, No Drawings

4,514,547

2-HYDROXYPROPANE SULPHONIC ACID DERIVATIVES: THEIR PREPARATION AND CURABLE COMPOSITIONS THEREOF

FIELD OF THE INVENTION

This invention relates to 2-hydroxypropane sulphonic acid derivatives, processes for their preparation and curable compositions containing them.

BACKGROUND OF THE INVENTION

U.K. Pat. No. 1,059,984 discloses 2-hydroxyalkane sulphonic acids and their salts, and their preparation from a bisulphite of a nitrogen base and an alkylene oxide such as ethylene oxide, propylene oxide or butylene oxide. The bisulphite of the nitrogen base and the alkylene oxide are water-soluble and their reaction is effected in aqueous solution.

In U.K. Pat. No. 983,049 there is disclosed a process in which epoxy compounds, including glycidyl alkyl ethers and glycidyl carboxylic acid esters, are reacted with adducts of a bisulphite with an oxo compound, e.g., 2-hydroxypropane-2-sulphonic acid, formed by reaction of sodium bisulphite with acetone. Preferred expoxy compounds are those containing 8 to 30 carbon atoms. The resulting sulphonated derivatives possess surface-active properties and are described as suitable for use as detergents and/or wetting agents. No mention is made of any epoxy compounds containing more than one epoxy group per molecule.

U.K. Pat. No. 1,310,672 describes a process for sulphonating alkyl or polyoxyalkylene glycidyl ethers by reaction with an organic carbonyl bisulphite adduct at an initial pH of from 6 to 8 and at elevated temperature. The bisulphite adduct is formed by reaction of sodium bisulphite with an aqueous aldehyde or ketone, preferably acetone. The resulting sulphonates are surfactants useful as ingredients of detergents and other washing compositions.

The three U.K. patents referred to above all relate to sulphonation of epoxy compounds containing a single epoxy group per molecule. U.K. Pat. No. 1,530,649 discloses sulphonation of a copolymer of an ethylenically unsaturated monomer, such as styrene or methylmethacrylate, with a glycidyl ester of an α-unsaturated carboxylic acid, such as glycidyl acrylate or glycidyl methacrylate. Sulphonation is achieved by reaction of the polymer in aqueous medium with sulphite ions of a water-soluble inorganic sulphite, e.g., sodium sulphite. Phase separation exists between the epoxy group-containing polymer and the aqueous solution, so sulphonation is effected in the presence of an ionic surface active agent, preferably a quaternary ammonium salt, e.g., tetra-n-butyl ammonium bisulphate, bromide, chloride or iodide. Reaction of the epoxy groups is slow and may be incomplete. Thus in the first example after 6 hours only 50% of epoxy groups had been converted to sulphonate groups, in the second example after 7 hours 96% had been converted, and in the third example after 4 hours 62% had been sulphonated. The resulting sulphonated polymers are soluble or dispersible in water and have potential application as thickeners, impregnating materials, binders, surface coating materials, adhesives, antistatic agents, ion-exchange resins and polymeric catalysts.

SUMMARY OF THE INVENTION

The present invention is directed to the preparation of 2-hydroxypropane sulphonic acid derivatives of epoxy resins wherein bifunctional epoxy resins are reacted with ammonium sulfites or bisulfites. These derivatives are water- and solvent-soluble binders capable of reacting with co-curing resins under mild storing conditions to produce films having high solvent resistance at ambient temperatures.

DESCRIPTION OF THE PREFERRED EMBODIMENTS

According to the present invention there is provided a 2-hydroxypropane sulphonic acid derivative of general formula

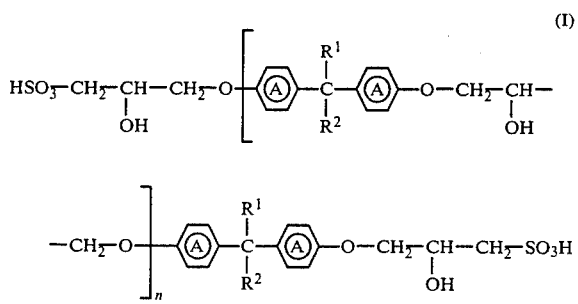

wherein n is a number having an average value from 0 to 12, Ⓐ denotes saturation of aromatic unsaturation in an associated carbocyclic ring and each of the $R^1$ and $R^2$ groups are independently selected from hydrogen and $C_{1-12}$ alkyl groups provided that each —C($R^1$)($R^2$)- group contains not more than 13 carbon atoms; or a salt thereof.

The compounds of formula I may be in the form of the free acid or in the form of a salt thereof. When prepared by a process to be described hereinafter, the initial product according to the invention is a tertiary or quaternary ammonium salt, which may readily be converted to the corresponding free acid by addition of a strong acid. Other salts, e.g., potassium and sodium salts, may readily be prepared from the tertiary or quaternary ammonium salt, or from the free acid. The term salt includes partially neutralized acid as well as fully neutralized derivative.

Preferred compounds of formula I are those wherein each A moiety denotes aromatic unsaturation. It is further preferred for n to have an average value from 0 to 9. When n is greater than 0, it will be appreciated that the groups —$CR^1R^2$— in the molecule may be the same or different. Conveniently all the groups $R^1$ and $R^2$ are methyl groups. When the $R^1$ and $R^2$ groups on a —$CR^1R^2$-moiety are not both methyl groups, it is preferred for one of $R^1$ and $R^2$ to be hydrogen, and the other to be a $C_{6-12}$ alkyl group. Thus, for example, one or more groups —$CR^1R^2$— in a molecule may conveniently be —$C(CH_3)_2$-groups while in another one or more such groups one of $R^1$ and $R^2$ may be hydrogen, the other being a $C_{6-12}$ alkyl group.

The invention also provides a process for preparing a 2-hydroxypropane sulphonic acid derivative of the invention wherein an epoxy resin of general formula

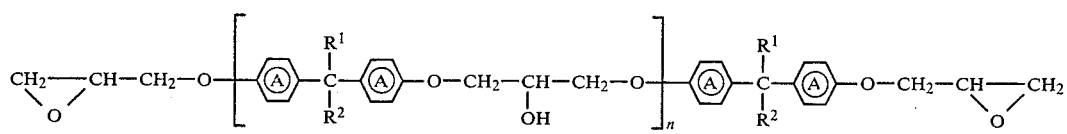 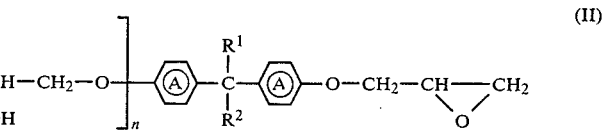

wherein $R^1$, $R^2$, n and Ⓐ are as defined above, is reacted with an ammonium sulphite or bisulphite of formula

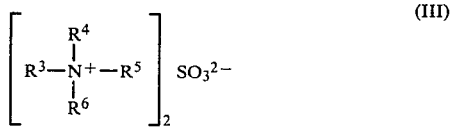

or

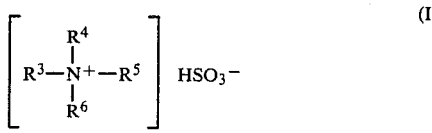

wherein $R^3$ is hydrogen and either $R^4$, $R^5$ and $R^6$ are independently selected from $C_{1-6}$ alkyl and 2-hydroxyalkyl groups or $R^4$ is a benzyl group optionally substituted by a methyl, methoxy or trifluoromethyl group and/or one or more halogen atoms or nitro groups and $R^5$ is a methyl group and $R^6$ is a methyl, ethyl or 2-hydroxyethyl group, provided that the total number of carbon atoms in the groups $R^4$, $R^5$ and $R^6$ does not exceed 10; or $R^3$, $R^4$, $R^5$ and $R^6$ are independently $C_{1-4}$ alkyl groups; or $R^3$, $R^4$ and $R^5$ are methyl groups and $R^6$ is a benzyl group or a $C_{5-16}$ alkyl group; in homogenous solution in an inert solvent, optionally followed by evaporation of the solvent to isolate the corresponding ammonium salt of the sulphonic acid of formula I, or by addition of a strong acid followed by separation of the precipitated free acid, or by conversion of the ammonium salt or the free acid to a desired salt.

Compounds of formula II are either well known compounds, or can be made from known compounds by analogous processes to those used for preparing known compounds, see for example U.S. Pat. No. 2,633,458 and U.S. patent application Ser. No. 440,647, filed Nov. 10, 1982 now U.S. Pat. No. 4,412,056, issued Oct. 25, 1983. Particularly preferred compounds of formula II, wherein A denotes aromatic unsaturation and all the $R^1$ and $R^2$ groups are methyl groups, are polyglycidyl ethers of 2,2-(4-hydroxypheny)propane. Polyglycidyl ethers which have molecular weights below 500 are also known as liquid epoxy resins, and those with higher molecular weights as solid epoxy resins.

Although the expected product of the process of the invention is a 2-hydroxypropane sulphonic acid derivative, in some cases amounts of product wherein the sulphonic acid moiety is attached at the 2-position and the hydroxy group is at the 1-position may also be produced and be present in the derivatives according to the invention.

The ammonium sulphites and bisulphites of formulae III and IV are based on tertiary amines or quaternary ammonium compounds, and are readily prepared by passing gaseous sulphur dioxide into a solution of the tertiary amine or the quaternary ammonium hydroxide in an inert solvent, e.g., 2-n-butoxyethanol, in the presence of water, in the case of tertiary amines. 2-Dimethyl-amino-2-methyl-1-propanol is a very suitable tertiary amine. Other suitable tertiary amines include triethylamine, tripropylamine, dimethylethanolamine, diethylethanolamine or triethanolamine. Suitable quaternary ammonium hydroxides include tetramethylammonium hydroxide, tetrabutylammonium hydroxide, tetramethylbenzylammonium hydroxide and cetyl trimethylammonium hydroxide.

The inert solvent in which the process of the invention is effected may be a single solvent or a mixture of two or more cosolvents. 2-n-butoxyethanol has been found to be a very suitable solvent.

During the course of the process of the invention the temperature of the homogenous solution is conveniently brought into the range from 50° C. to its reflux temperature.

Suitable strong acids include, for example, hydrochloric acid, hydrobromic acid and sulphuric acid.

The ammonium salt or the free acid may conveniently be converted to the desired salt by treating the ammonium salt with an appropriate metal oxide or hydroxide, or by neutralizing, or partially neutralizing, the acid in aqueous medium with an appropriate metal oxide or hydroxide, e.g., potassium or sodium hydroxide, or with an amine or a quaternary ammonium hydoxirde.

2-Hydroxypropane sulphonic acid derivatives of the invention are curable binders. Accordingly, the invention further comprises curable compositions comprising a 2-hydroxypropane sulphonic acid of formula I or a salt thereof and a co-curing resin. Suitable co-curing resins include, for example, urea-formaldehyde resins, melamine-formaldehyde resins, benzo-guanamine-formaldehyde resins and phenolic resins. The co-curing resins may be used in binder/co-curing resin weight ratios known in the art, for example in binder/co-curing resin weight ratios 95:5 to 60:40.

The curable compositions are particularly suitable for use as thermosetting coating compositions. The compositions may generally be diluted with, and may themselves contain, polar non-aqueous solvents, for example 2-n-butoxyethanol.

2-Hydroxypropane sulphonic acids of formula I and their salts are water thinnable, i.e., they may be diluted with water, in the absence of any surfactant or emulsion stabilizer, to give stable aqueous solutions or dispersions. Accordingly, thermosetting coating compositions based on acids of formula I or their salts may be aqueous compositions. Such aqueous compositions are conveniently prepared by diluting the acid of formula I or a salt thereof with water to 10% to 30% by weight solids content and adding a water-soluble or water-miscible co-curing resin, although the co-curing resin may be added before dilution with water.

Coating compositions of the invention may additionally contain conventional paint additives, such as pigments, fillers, plasticizers and thixotropic agents.

Coating compositions of the invention may be applied to a suitable substrate, e.g., steel, tinplate, aluminum or wood, by any suitable means such as brush, blade, roller, spray or dip. In addition, the aqeuous coating compositions may be applied to electrically conductive substrates by electrophoretic deposition. The resulting coatings may be cured by heating at conventional temperatures for conventional periods of time, for example for a metal substrate from 80° to 200° C. for 2 to 10 minutes. For a wood substrate curing will be at lower temperatures for longer times, e.g., 40° to 70° C. for 15 minutes to 18 hours.

The invention will be further described in the following illustrative examples. Parts and percentages are by weight unless otherwise designated.

EXAMPLES 1 to 4

Preparation of 2-hydroxypropane sulphonic acids (a) Preparation of N,N dimethyl-N-(1-hydroxy-2-methylprop-2-yl) ammonium sulphite and bisulphite DMAMP-80 (14.8 g, 100 mmol) (DMAMP-80 is an 80% w/w solution of 2-dimethylamino-2-methyl-1-propanol in water) was dissolved in 2-n-butoxyethanol (20 g). The resulting solution was cooled to 0° C. and gaseous sulphur dioxide (3.2 g, 50 mmol) was passed in to yield a solution containing N,N-dimethyl-N-(1-hydroxy-2-methyl-prop-2-yl)ammonium sulphite in equilibrium with the bisulphite.

(b) Preparation of 2-hydroxypropane sulphonates

A chosen polyepoxide (25 mmol, ½×epoxy molar mass(g)) was dissolved in 2-n-butoxyethanol to give a solution having a solids content from 50% to 60% by weight. This solution was added dropwise at 0° C., with stirring, to the solution from step (a). The temperature of the resulting reaction mixture was gradually raised to from 50° C. to reflux temperature. It is preferred to use higher temperatures within the range 50° C. to reflux temperature with polyepoxides of higher epoxy molar mass. Reaction was continued until aliquots, which were taken from the reaction mixture at regular intervals, appeared to be water-dilutable. Reaction time was generally of the order of 3 hours. The resulting solution contained the N,N-dimethyl-N-(1-hydroxy-2-methyl-prop-2-yl) ammonium salt of the 2-hydroxypropane sulphonic acid.

Dilution of portions of the solutions with water to 10% w solids content and subjection to electrodeposition at electrode distance 3 cm and 200V deposition voltage gave only anodic deposition, confirming that water-solubility is conferred by reaction between epoxy and sulphite moieties and not between epoxy and amine moieties. Infrared spectra of the solutions were fully in accordance with the expected structures.

(c) Preparation of 2-hydroxypropane sulphonic acids

The resulting solutions from step (b) were acidified with concentrated hydrochloric acid, whereupon the free acids precipitated out as clear to straw-colored precipitates. The precipitates were filtered off (or in some cases were isolated by decantation of supernatant liquid), washed with concentrated hydrochloric acid and dried to give the free acids as glassy solids. Acid contents of the free acids were determined by potentiometric titration.

The polyepoxides used were polyglycidyl ethers of 2,2-(4-hydroxyphenyl)propane commercially available under the registered Trade Mark "EPIKOTE". The code numbers of the polyepoxides, their epoxy group concentrations (EGC) (and epoxy molar masses (EMM)) and the acid contents of the resulting free acids from step (c) are given in Table I.

TABLE I

| Example | "EPIKOTE" Code No. | EGC (mmol/kg) (EMM(g)) | Acid content (m. equivalents/g) Calculated | Acid content (m. equivalents/g) Found |
|---|---|---|---|---|
| 1 | 828 | 5150–5490 (182–194) | 3.68 | not determined |
| 2 | 1001 | 2000–2220 (450–500) | 1.78 | 1.58 |
| 3 | 1055 | 1110–1250 (800–900) | 1.02 | 0.90 |
| 4 | 1007F | 796 (1256) | 0.75 | 0.46 |

EXAMPLE 5

After dilution with water to solids contents of 25% w, solutions containing N,N-dimethyl-N-(1-hydroxy-2-methylprop-2-yl) ammonium salts of the 2-hydroxypropane sulphonic acids of Examples 3 and 4 (binders) (from step (b)) were mixed at ambient temperature with water-soluble co-curing resins in binder/co-curing resin weight ratios from 95/5 to 70/30. No curing catalyst was added. The resulting lacquers were applied using a bar coater onto undegreased tinplate panels (quality E2, finish 311, thickness 0.23 mm) to give coatings having a film thickness after stoving of 5-6 μm. Stoving was effected in a forced air circulation oven.

Results, including binder/co-curing resin weight ratios, curing schedules (minutes/°C.), solvent resistance, pencil hardness and flexibility are given in Table II.

Solvent resistance is determined by rubbing the cured coating with a piece of cotton cloth soaked in methylethylketone and is expressed as the number of double rubs required to soften the surface (MEK rubs).

Flexibility of the cured coating is assessed by the wedge bend test, in which a coated tinplate panel is bent over a 3 mm mandrel and impacted into a wedge shape. The panel is then immersed in a $CuSO_4$/HCl solution for 2 minutes, whereby any breaks in the coating will become stained. The extent of staining as a % failure of the coating at the bend is recorded.

TABLE II

| Binder of Example | Co-curing resin | Binder/co-curing resin solids ratio | Curing Schedule min/°C. | MEK rubs | Pencil hardness | Wedge bend test (% failure) |
|---|---|---|---|---|---|---|
| 3 | hexa-methoxy-methyl-melamine | 95/5 | 5/200 | >>100 | — | 20 |
|   |   | 90/10 | 5/200 | >>100 | — | 25 |
|   |   | 85/15 | 5/200 | >>100 | — | 30 |
|   |   | 70/30 | 5/200 | >>100 | 5H | 40 |
|   |   |       | 5/180 | >>100 | 4H | 30 |

TABLE II-continued

| Binder of Example | Co-curing resin | Binder/co-curing resin solids ratio | Curing Schedule min/°C. | MEK rubs | Pencil hardness | Wedge bend test (% failure) |
|---|---|---|---|---|---|---|
| | | | 5/160 | >>100 | 2H | 25 |
| | | | 5/140 | >100 | 2H | 25 |
| | | | 5/130 | >100 | 1H | 22 |
| | | | 5/120 | >100 | 1H | 20 |
| | | | 5/110 | >100 | 1H | 20 |
| | | | 5/100 | >100 | 1H | 18 |
| | | | 5/90 | >100 | 1H | 15 |
| | | | 5/80 | 50 | F | 10 |
| | | | 15/80 | 100 | 1H | 15 |
| | | | 15/70 | 50 | F | 10 |
| | | | 30/70 | 100 | 1H | 10 |
| | | | 1080/40 | 50 | F | <5 |
| 3 | a phenol-formaldehyde resin ("IMPRENAL" LV 21/408) | 80/20 | 5/200 | >100 | — | 60 |
| | | | 5/180 | >100 | — | 45 |
| | | | 5/160 | >100 | — | 40 |
| | | | 5/140 | >100 | — | 30 |
| | ("IMPRENAL" is a registered Trade Mark) | 90/10 | 5/200 | >100 | — | 40 |
| | | | 5/180 | >100 | — | 35 |
| | | | 5/160 | >100 | — | 30 |
| | | | 5/140 | >100 | — | 25 |
| 4 | hexamethoxymethylmelamine | 90/10 | 5/200 | >100 | — | 25 |
| | | 70/30 | 5/200 | >100 | — | 30 |
| | "IMPRENAL" LV 21/408 | 90/10 | 5/200 | >100 | — | 30 |
| | | 80/20 | 5/200 | >100 | — | 35 |

In all cases adhesion of the cured coating to the surface of the tinplate was good.

EXAMPLE 6

The 2-hydroxypropane sulphonic acids (binders) of Examples 3 and 4 were dissolved in 2-n-butoxyethanol to give 25% w solutions which were mixed at ambient temperature with co-curing resins in binder/co-curing resin weight ratios from 90/10 to 70/30. No curing catalyst was added.

The resulting lacquers were applied to tinplate panels and the resulting coatings were tested, by procedures described in Example 5. Results are given in Table II.

TABLE III

| Binder of Example | Co-curing resin | Binder co-curing resin solids ratio | Curing Schedule min/°C. | MEK rubs | Wedge bend test (% failure) |
|---|---|---|---|---|---|
| 3 | hexamethoxymethyl melamine | 70/30 | 5/200 | >>100 | 60 |
| | | | 5/180 | >>100 | 50 |
| | | | 5/160 | >>100 | 40 |
| | | 90/10 | 5/200 | >>100 | 35 |
| | | | 5/180 | >>100 | 30 |
| | | | 5/160 | >>100 | 20 |
| 4 | hexamethoxymethyl melamine | 70/30 | 5/200 | >>100 | 40 |
| | | | 5/180 | >>100 | 35 |
| | | | 5/160 | >>100 | 25 |
| | | 90/10 | 5/200 | >>100 | 30 |
| | "IMPRENAL" LV 21/408 | 80/20 | 5/200 | >>100 | 40 |
| | | | 5/180 | >>100 | 30 |
| | | | 5/160 | >>100 | 25 |

In all cases adhesion of the cured coating to the surface of the tinplate was good.

What is claimed is:

1. A 2-hydroxypropane sulphonic acid derivative of general formula

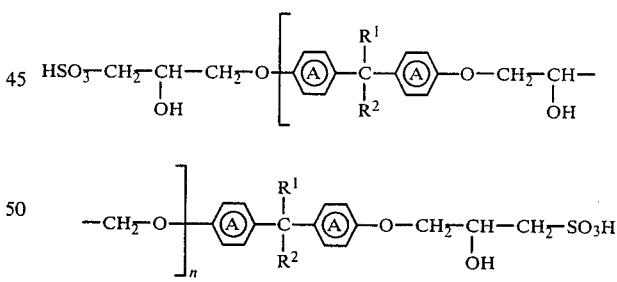

wherein n is a number having an average value from 0 to 12, (A) denotes saturation of aromatic unsaturation in an associated carbocyclic ring, and each of the $R^1$ and $R^2$ groups are independently selected from hydrogen and $C_{1-12}$ alkyl groups provided that each $—C(R^1)(R^2)—$ group contains not more than 13 carbon atoms; or a salt thereof.

2. The derivative of claim 1 wherein each A moiety denotes aromatic unsaturation, n has an average value from 0 to 9 and the $R^1$ and $R^2$ groups are methyl groups.

3. The derivative of claim 1 in the form of the free acid or a tertiary or quaternary ammonium salt thereof.

4. A process for preparing the derivative of claim 1 wherein an epoxy resin of general formula

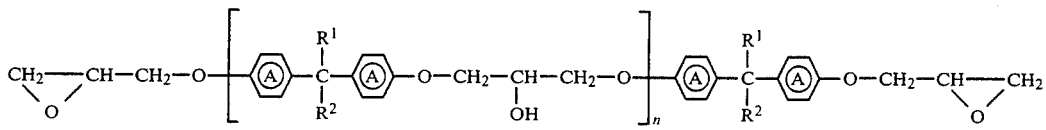

wherein $R^1$, $R^2$, n and A are as defined in claim 1, is reacted with an ammonium sulphite or bisulphite of formula

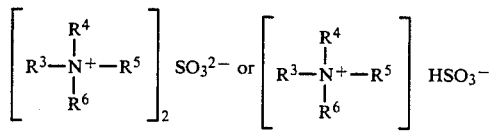

wherein $R^3$ is hydrogen and either $R^4$, $R^5$ and $R^6$ are independently, selected from $C_{1-6}$ alkyl and 2-hydroxyalkyl groups or $R^4$ is a benzyl group optionally substituted by a methyl, methoxy or trifluoromethyl group and/or one or more halogen atoms or nitro groups and $R^5$ is a methyl group and $R^6$ is a methyl, ethyl or 2-hydroxyethyl group, provided that the total number of carbon atoms in the groups $R^4$, $R^5$ and $R^6$ does not exceed 10; or $R^3$, $R^4$, $R^5$ and $R^6$ are independently $C_{1-4}$ alkyl groups; or $R^3$, $R^4$ and $R^5$ are methyl groups and $R^6$ is a benzyl group or a $C_{5-16}$ alkyl group in homogeneous solution in an inert solvent, followed by evaporation of the solvent to isolate the corresponding ammonium salt of the sulphonic acid derivative.

5. A curable composition comprising a 2-hydroxypropane sulphonic acid derivative of claim 1 or a salt thereof and a synthetic co-curing resin selected from the group consisting of urea-formaldehyde resins, melamine-formaldehyde resins, benzo-guanamine-formaldehyde resins and phenolic resins.

6. A curable composition of claim 5 wherein the co-curing resin is a melamine-formaldehyde resin.

7. The curable composition of claim 6 wherein the melamine-formaldehyde resin is hexamethoxymethylmelamine.

8. The process of claim 4 wherein the ammonium salt is converted to the corresponding free acid by the addition of a strong acid followed by the separation of the precipitated free acid.

9. The process of claim 4 wherein the ammonium salt is converted to the corresponding sodium or potassium salt with an appropriate metal oxide or hydroxide.

* * * * *